United States Patent [19]

Hoeschele

[11] 4,207,416
[45] Jun. 10, 1980

[54] ETHYLENEDIAMINEPLATINUM(II) 2,4-DIOXOPYRIMIDINE COMPLEXES

[75] Inventor: James D. Hoeschele, Piscataway, N.J.

[73] Assignee: Engelhard Minerals & Chemicals Corporation, Iselin, N.J.

[21] Appl. No.: 888,802

[22] Filed: Mar. 21, 1978

Related U.S. Application Data

[60] Division of Ser. No. 651,141, Jan. 21, 1976, Pat. No. 4,080,324, which is a continuation of Ser. No. 503,585, Sep. 5, 1974, abandoned.

[51] Int. Cl.² ............... C07H 19/06; C07H 19/10; C07F 15/00
[52] U.S. Cl. ........................................ 536/23
[58] Field of Search ............................. 536/23

[56] References Cited

U.S. PATENT DOCUMENTS 4,080,324  3/1978  Hoeschele ............... 536/23

OTHER PUBLICATIONS

Cleare et al., Coordination Chemistry Reviews, vol. 12, pp. 349 and 399–405, Jun. 1974.
Connors et al., Platinum Coordin. Complexes in Cancer Chemother., title pp. IX, XI, XII, 40–41, 51–52, 61, 66, 84–89, 135 and list of participants (Jun. 1974).
Rosenberg, Die Naturwissenschaften, vol. 60, pp. 399–406 (1973).
Gelaman et al., Russian J. of Inorganic Chemistry, vol. 5, p. 1602 (1970).
Mansy et al., J. Am. Chem. Soc., vol. 95, pp. 1633–1646 (1973).

*Primary Examiner*—John D. Randolph

[57] ABSTRACT

Ethylenediamineplatinum(II) 2,4-dioxopyrimidine complexes are characterized by high anti-tumor activity and low mammalian toxicity.

6 Claims, 6 Drawing Figures

ETHYLENEDIAMINEPLATINUM(II) 2,4-DIOXOPYRIMIDINE COMPLEXES

CROSS-REFERENCES TO RELATED APPLICATIONS

This is a division of application Ser. No. 651,141 filed Jan. 21, 1976, now U.S. Pat. No. 4,080,324, issued on Mar. 21, 1978, which is in turn a continuation of application Ser. No. 503,585, filed Sept. 5, 1974, and abandoned.

This invention is concerned with certain 2,4-dioxopyrimidine complexes of platinum(II) compounds, as well as the use of such complexes as chemotherapeutic agents. More particularly, this invention is concerned with complexes of uracil and its derivatives with platinum(II) compounds which vary from white or off-white to tan in color, and are hereinafter referred to as "platinum tans", and which are characterized by pronounced activity against tumors combined with low animal toxicity.

Recently, Rosenberg et al reported the discovery that certain platinum coordination compounds were of interest as anti-tumor agents. (Rosenberg et al., "Platinum Compounds: A New Class of Potent Antitumour Agents," Nature, Vol. 222, Apr. 26, 1969) pp. 385–6.) Since then, considerable effort has been expended to evaluate various classes of coordination complexes for similar activity. See, e.g. M. J. Cleare, "Transition Metal Complexes in Cancer Chemotherapy," Coordination Chemistry Reviews, 12 (1974) pp. 349–405. One such class of compounds reported by Cleare comprises the so-called "platinum blues", which are blue-colored complexes of uracil and related compounds with inorganic platinum(II) compounds, especially a diammine-uracil complex formed from hydrolyzed cis-diamminedichloroplatinum and uracil.

In accordance with the present invention, there is provided a novel class of non-blue complexes of uracil and platinum(II) compounds which have exhibited pronounced antitumor activity but are less toxic than the "platinum blues". This novel class of non-blue complexes or "platinum tans comprises ethylenediamineplatinum(II) 2,4-dioxopyrimidine complexes.

The 2,4-dioxopyrimidines which constitute one moiety of the complexes of this invention are represented by the formula:

wherein R is hydrogen, lower alkyl or a saccharide moiety, and each of $R^1$ and $R^2$, independently is hydrogen, halogen, lower alkyl, carboxyl, lower alkoxycarbonyl, hydroxy, and lower alkoxy, as well as the dihydro derivatives of the 2,4-dioxopyrimidines. By the term "lower alkyl", as employed herein, is meant a linear or branched chain alkyl group of from 1 to about 6 carbons, and preferably from 1 to about 3 carbons, such as methyl, ethyl and propyl. By the term "lower alkoxy" is meant a linear or branched chain alkoxy group of from 1 to about 6 carbons, and preferably from 1 to about 3 carbons, such as methoxy, ethoxy and propoxy. The term "halogen" is intended to embrace fluorine, chlorine, bromine and iodine. Illustrative 2,4-dioxopyrimidine derivatives include uracil ($R=R^1=R^2=H$), thymine or 5-methyluracil ($R=R^1=H$; $R^2=$Methyl), 6-methyluracil ($R=R^2=H$; $R^1=$Methyl), 5,6-dimethyluracil ($R=H$; $R^1=R^2=$Methyl), 5-fluorouracil ($R=R^1=H$; $R^2=F$), uridine ($R^1=R^2=H$; $R=$Ribosyl), thymidine ($R=$Ribosyl; $R^2=$Methyl; $R^1=H$), dihydrouracil, and the like. It is to be understood that uracil and its derivatives may exist in enol-keto tautomeric forms, all of which are encompassed by this invention.

The remainder of the platinum tan complex comprises an ethylenediamineplatinum(II) moiety wherein the ethylenediamine is represented by the formula:

wherein each of $R^3$, $R^4$, $R^5$, $R^6$, $R^7$ and $R^8$ is hydrogen or lower alkyl. Preferred are the ethylenediamines wherein at least five of said $R^3$, $R^4$, $R^5$, $R^6$, $R^7$ and $R^8$ are hydrogen. Illustrative examples of suitable compounds include ethylenediamine, 1,2-propylenediamine, 1,2-butylenediamine, 2,3-butylenediamine, N-methylethylenediamine, N,N'-dimethylethylenediamine and the like.

The complexes of this invention are prepared by reacting a diaquoethylenediamine platinum(II) salt, preferably the nitrate salt, with a 2,4-dioxopyrimidine in aqueous medium. The starting salt may be represented by the formula:

wherein $R^3$–$R^8$ are as defined above; X is an anion; and n is a number having a value of 0 or 1. X may be any suitable anion, such as sulfate, nitrate, perchlorate or bicarbonate, although nitrate is preferred. Anions having greater complexing ability than water or the dioxopyrimidine, such as chloride, iodide and bromide, are not suitable.

The diaquo salt may be formed by the stoichiometric reaction of an ethylenediaminedichloroplatinum(II) compound with silver nitrate in aqueous medium at room temperature. On concentration and crystallization of the product, there is obtained a product of the formula:

The diaquoethylenediamineplatinum(II) salt and the dioxopyrimidine are reacted in approximately equimolar amounts, and it is preferred that the molar ratio of platinum(II) to dioxopyrimidine be in the range of from about 0.8:1 to about 1.2:1. The concentration of the reactants is not highly critical, and ordinarily the concentration of the platinum compound is of the order of from about 0.02 to about 0.05 molar. It is desired that the initial pH of the reaction mixture be about neutral. No further pH adjustment is necessary, although the reaction mixture becomes acidic as the reaction proceeds, falling to a pH of about 2.5 to 3.0 on completion. If desired, the pH of the reaction may be maintained at a higher pH or even at neutral pH by the addition of a suitable base, preferably an alkali metal hydroxide such as sodium hydroxide or potassium hydroxide.

Upon completion of the reaction, the complex of this invention is recovered by addition of a water-miscible organic solvent, for example an alcohol such as ethanol or propanol. As a result, the complex precipitates from the reaction mixture and it can be recovered by conventional solid-liquid separation procedures.

The complexes of this invention, in contrast to those of Rosenberg, are not blue in color. Rather, they vary from tan to off-white in color, and hence are referred to herein as platinum tans. The complexes of this invention are further characterized by ultraviolet spectra having absorption maxima at about 200 nm (198–201 nm) and about 288 nm (287–290 nm) and an absorption minimum at about 254 nm (251–256 nm).

The complexes of this invention are of particular utility in tumor chemotherapy, having been found active against sarcoma 180 ascites in mice. The complex is administered interperitoneally as an aqueous solution in generally known manner. The solution may contain other components, such as physiologically-acceptable salts, other medicaments, etc. The dosage level required to act as an anti-tumor agent is not narrowly critical, and indeed it is a feature of the complexes of this invention that, because they are relatively non-toxic, they may be administered over a wide dosage range. The specific dosage level will vary from compound to compound, but ordinarily effective results against S 180 in mice have been achieved at a dosage of from 20 to as high as 2000 milligrams of complex per kilogram of body weight.

EXAMPLE I

Ethylenediamineplatinum(II)Uracil Complex

A 0.1 molar stock solution of diaquoethylenediamineplatinum(II) nitrate prepared by reacting $AgNO_3$ with dichloroethylenediamineplatinum(II) was diluted with water (four-fold) and the pH of the solution was adjusted to 7.0 using 2 N NaOH. Uracil was added to give a uracil to platinum(II) molar ratio of 1 and, after dissolution, the pH was readjusted to 7.0. This solution was then diluted to give a final Pt(II) concentration of 0.02 M and the reaction flask was placed in a thermostatted bath at 40° C. for 2–4 weeks. During this time, the flask was loosely capped to allow free entry of air. On completion of the reaction, the yellowish solution (pH 2.5) was concentrated approximately 25 times by means of a flash evaporator and absolute ethanol was added to the concentrate to the point of incipient precipitation when the mixture just became cloudy. The aqueous-alcoholic mixture was then placed in a freezer overnight and a first crop of product was filtered out the next day. The precipitate was washed with a cold ethanol-water mixture having 5–10% greater alcohol content than the filtrate and then cold absolute ethanol. The product was air-dried and then dried in vacuo at room temperature to yield 3.22 grams of light tan solid complex. Three additional crops were obtained through the successive addition of absolute ethanol to the filtrate from a preceeding crop until incipient precipitation, followed by the recovery of the precipitate as described above. A total of 5.34 grams of product was obtained.

Elemental analysis of the complex gave the following results: Pt, 45.86%; C, 16.76%; H, 2.75%; N, 15.21%; O, 19.57%.

Ultraviolet analysis of the first three crops of the complex gave the following results:

| Crop | λ max, nm | Absorptivity ($\epsilon$), ml/mg — cm | | λmin, nm | Absorbance at 200 ± 2nm |
|---|---|---|---|---|---|
| | | 200 ± 2nm | 288 ± 2nm | | Absorbance at 288 ± 2nm |
| 1 | 198–201,288 | 56.0 | 13.9 | 256 | 4.04 |
| 2 | 198–201,287 | 61.6 | 15.1 | 254 | 4.08 |
| 3 | 198–201,286.7 | 55.7 | 13.0 | 253 | 4.27 |

EXAMPLE II

Ethylenediamineplatinum(II) Uracil Complex

The procedure of Example I was repeated, except that the concentration of Pt(II) prior to the addition of uracil was 0.05 M and sodium hydroxide was added periodically (to a total of 0.47 meq. NaOH/m mole Pt) to readjust the pH of reaction mixture to 7. Six crops of product were obtained, weighing a total of 1.93 grams.

Elemental analysis: Pt, 47.02%; C, 17.48%; H, 2.90%; N, 13.64%; O, 19.15%.

Ultraviolet analysis of each of the six crops gave the following results:

| Crop | λmax, nm | Absorptivity ($\epsilon$), ml/mg — cm | | λmin, nm | Absorbance at 200 ± nm |
|---|---|---|---|---|---|
| | | 200 ± nm | 288 ± nm | | Absorbance at 288 ± nm |
| 1 | 198–201,288 | 50.5 | 19.8 | 255 | 2.55 |
| 2 | 198–201,287 | 50.3 | 19.6 | 254 | 2.56 |
| 3 | 198–201,289 | 49.6 | 18.7 | 252 | 2.66 |
| 4 | 198–201,288 | 50.3 | 18.7 | 251 | 2.70 |
| 5 | 198–201,288 | 51.7 | 18.2 | 248 | 2.84 |
| 6 | 198–201,287 | 42.5 | 32.7 | 247 | 1.30 |

EXAMPLE III

Ethylenediamineplatinum(II) 5-Fluorouracil Complex

Employing procedures similar to those described in Example II, except that 5-fluorouracil was substituted for uracil, 3.05 grams of the 5-fluorouracil complex was obtained in two crops.

Elemental analysis: Pt, 46.45%; C, 17.21%; H, 2.81%; N, 13.61%; F, 4.47%; O (by difference), 15.45%.

EXAMPLE IV

Ethylenediamineplatinum(II) Thymine Complex

Employing procedures similar to those described in Example II, except that thymine was substituted for uracil, 1.75 grams of the thymine complex was obtained in one crop.

Elemental analysis: Pt, 48.61%; C, 18.21%; H, 3.06%; N, 13.94%; O, 16.39%.

Ultraviolet analysis of the product gave the following results:

$\lambda_{max}$, at 197 and 293 nm
$\lambda_{min}$ at 260 nm
Absorptivity at:
197 nm-46.5
293 nm-12.8

EXAMPLE V

Ethylenediamineplatinum(II) Uridine Complex

Employing procedures similar to those described in Example II, except that uridine was substituted for uracil, the uridine complex was obtained.

Elemental analysis: Pt, 37.50%; C, 21.22%; H, 3.94%; N, 10.59%; O, 27.15%.

Samples of each of the crops of complexes prepared as described in Examples I-V were tested for antitumor activity against S180 in female Swiss white mice by the following procedure:

CFW mice, averaging 20 g, are immediately inspected, weighed, and then placed in newly prepared cages (6 mice/cage or 1 set). On day 0 the mice are inoculated with 0.2 ml of a freshly prepared saline suspension (0.15 M NaCl) containing $1 \times 10^7$ tumor cells/ml or a total of $2 \times 10^6$ cells. This inoculum is freshly prepared using "transfer" mice which have been injected with tumor cells the previous week. This inoculum is the end-product of a series of steps which involves (1) the removal of the cells from the peritoneal cavity of the sacrificed transfer mouse, (2) alternate centrifugation-washing (2-3 times with cold saline) to remove occasional blood and other undesirable components, and finally (3) dilution (1:3) of the packed cell volume with saline (the final centrifugation being carried out at 1000 rpm for 2 min.). A cell count is made (in duplicate) on a 100-fold dilution of this 1:3 suspension (nominally $\sim 5 \times 10^7$ cells/ml) by means of a hemacytometer counting chamber and a microscope. A final dilution to $1 \times 10^7$ cells/ml is made based on the averaged count (normally $\sim$ 500-600 cells are counted to obtain reliable statistics). On day 1 solutions of the test compounds are prepared and the mice injected, with each mouse of a set of six mice being injected with the same test compound at the same dosage level. The doses are based on the average wt. of the animals (cage weights).

Also, on this day three types of control are employed: (1) Normal (1 set): 0.5 ml of water; (2) Positive Control (1 set): a known antitumor agent (cis-dichlorodiammineplatinum (II)) is continually used to serve as a check on the response of the biological test system, cis-[Pt(NH$_3$)$_2$Cl$_2$] at 7 mg/kg; (3) Negative Control (1 set): the negative control mice receive no additional injections.

The effectiveness of a compound is measured in terms of the % increase in life span of the test animals relative to the controls (calculated from the day of tumor inoculation (day 0)). In order to standardize the test data and permit intercomparisons to be made, the day of evaluation is arbitarily taken as that day corresponding to twice the mean life-span (or average day of death) of the controls. This sets a practical upper limit of 100% on the % ILS attainable. For calculational purposes survivors on the day of evaluation are considered to have died on that day. The % ILS is formulated as:

$$\% \, ILS = \left( \frac{\text{mean life-span of test mice}}{\text{mean life-span of control mice}} - 1 \right) \times 100\%$$

The increase in life span, in percent over controls, is tabulated against dosage for each of the complexes as follows:

Table I

| | Uracil Complex of Example I | | |
|---|---|---|---|
| | Increase in Life Span, % | | |
| Dosage, mg/kg | Crop 1 | Crop 2 | Crop 3 |
| 20 | 16 | — | 11 |
| 40 | 16 | — | 51 |
| 80 | 56 | — | 70 |
| 100 | 92 | — | 93 |
| 160 | 94 | — | 100 |
| 200 | 90 | — | 83,100 |
| 300 | — | — | 42 |
| 320 | — | — | 100 |
| 400 | 84 | — | 100,67 |
| 600 | 100 | — | −47 |
| 800 | — | — | −67 |

From the foregoing data, it is evident that the threshold of activity of this complex was around 20 to 40 mg/kg, while maximum activity (100% ILS) was observed at 400 mg/kg (Crop 3) to 600 mg/kg (Crop 1). Toxicity was found at 600 mg/kg for Crop 3 and at 800 mg/kg for Crop 1. The LD$_{50}$ for Crop 3 was about 400-500 km/kg. Long term survivors (of at least 38-54 days) were observed with each crop.

Table II

| | Uracil Complex of Example II | | | | |
|---|---|---|---|---|---|
| Dosage, | Increase in Life Span, % | | | | |
| mg/kg | Crop 1 | Crop 2 | Crop 3 | Crop 4 | Crop 5 |
| 20 | 6 | — | — | — | — |
| 40 | 14 | 1 | — | — | — |
| 80 | 19 | 19 | — | — | — |
| 150 | — | 17 | — | — | — |
| 160 | 13 | 15 | — | — | — |
| 200 | — | — | — | — | 10 |
| 300 | — | 31 | — | — | — |
| 320 | — | 16 | — | — | — |
| 400 | — | — | — | — | 16 |
| 450 | — | 48 | — | — | — |
| 500 | — | — | 31 | — | — |
| 600 | — | 75 | — | — | — |
| 750 | — | — | 38 | — | — |
| 1000 | — | — | 47 | — | — |

From the foregoing data, it is evident that the uracil complex prepared at a more constant pH of about 7 had a higher threshold of activity (about 800 mg/kg) than the complex prepared without adjustment of pH. No acute toxicity was observed, even at the highest dosage level tested.

Table III

| 5-Fluorouracil Complex of Example III | |
|---|---|
| Dosage, mg/kg | Increase in Life Span, % Crop 1 |
| 50 | 13 |
| 100 | 3 |
| 200 | 5 |
| 400 | 32 |
| 600 | 31 |
| 800 | 29 |
| 1000 | 62 |
| 1600 | 76 |

The 5-fluorouracil complex exhibits activity with no evidence of acute toxicity in the range of 1000 to 1600 mg/kg.

Table IV

| Thymine Complex of Example IV | |
|---|---|
| Dosage, mg/kg | Increase in Life Span, % Crop 2 |
| 100 | 35 |
| 200 | 100 |
| 400 | 100 |
| 800 | 100 |
| 1600 | 100 |
| 2000 | 100 |

The thymine complex is characterized by pronounced activity over a large (20-fold) dosage range with no evidence of actue toxicity in this range. Long term survivors (of 52 to 60 days) were observed in the tests at the 200, 400 and 800 mg/kg dosage levels.

Table V

| Uridine Complex of Example V | |
|---|---|
| Dosage, mg/kg | Increase in Life Span, % |
| 200 | 69 |
| 400 | 76 |
| 600 | 90 |
| 800 | 100 |
| 1200 | 100 |

Figure 1:
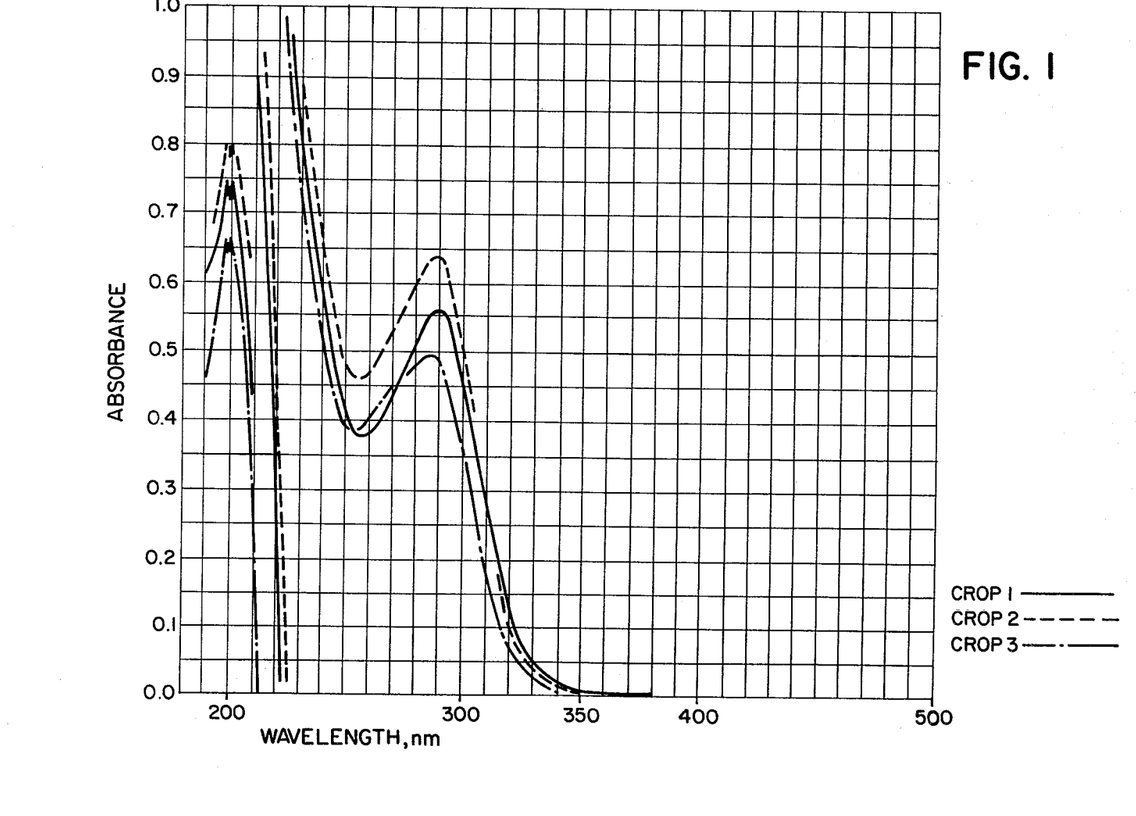
Figure 2:
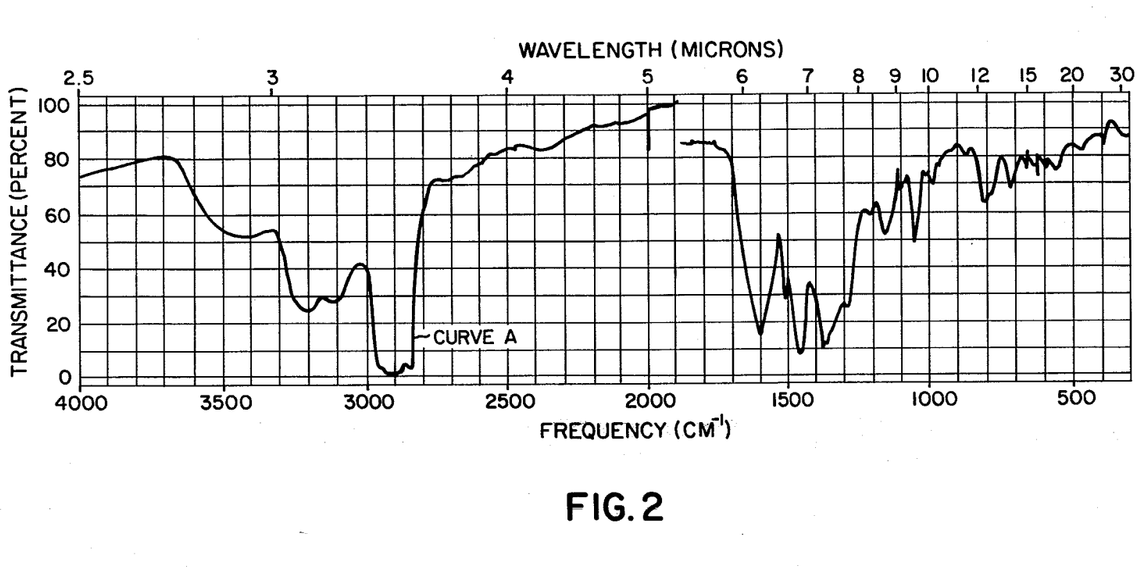

The complete ultraviolet spectra for each of the three crops of the product of Example I are reproduced in FIG. 1, and the infra-red spectrum for a uracil complex prepared in a similar manner to that of Example I is reproduced as the curve (Curve A) in FIG. 2.

Figure 3:
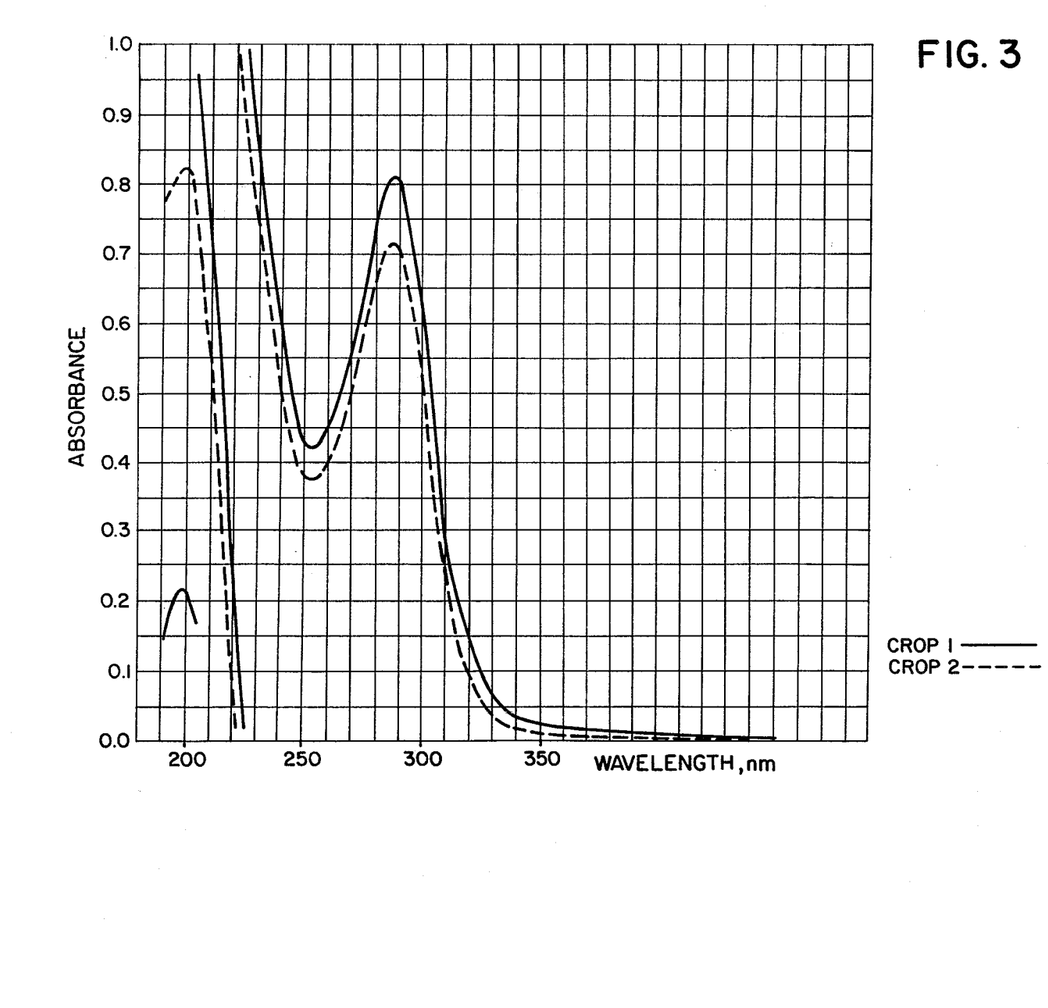
Figure 4:
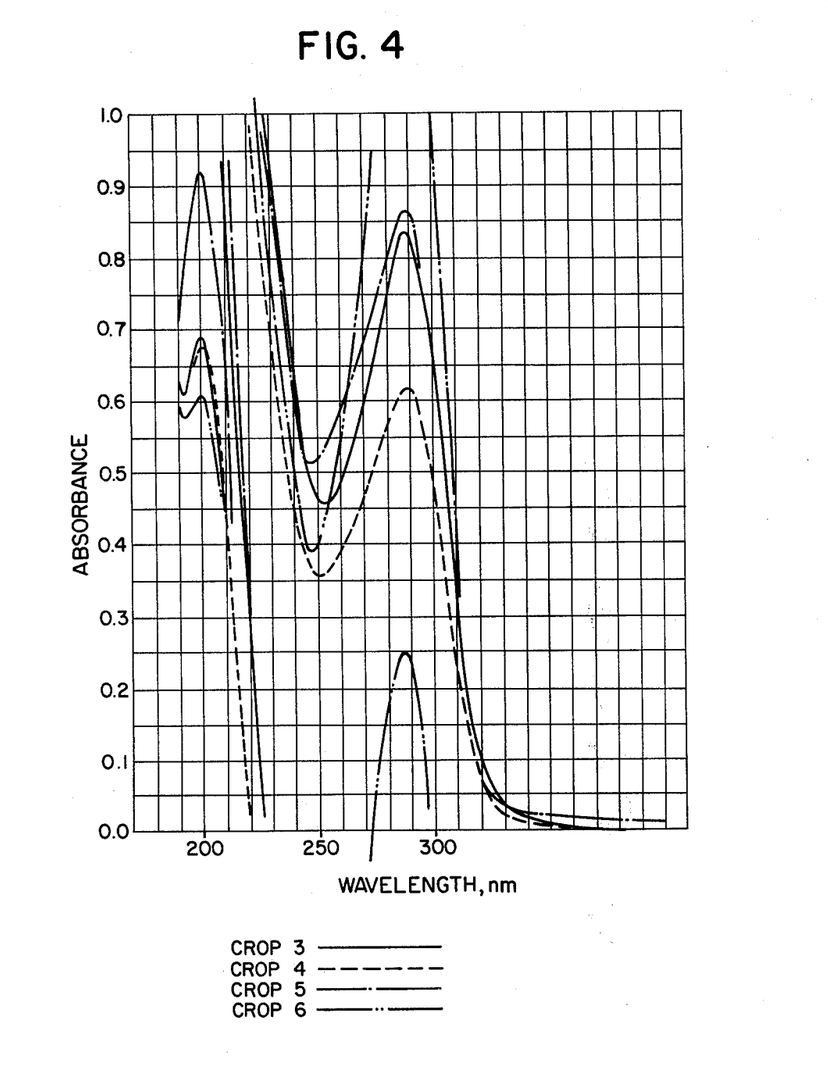
Figure 5:
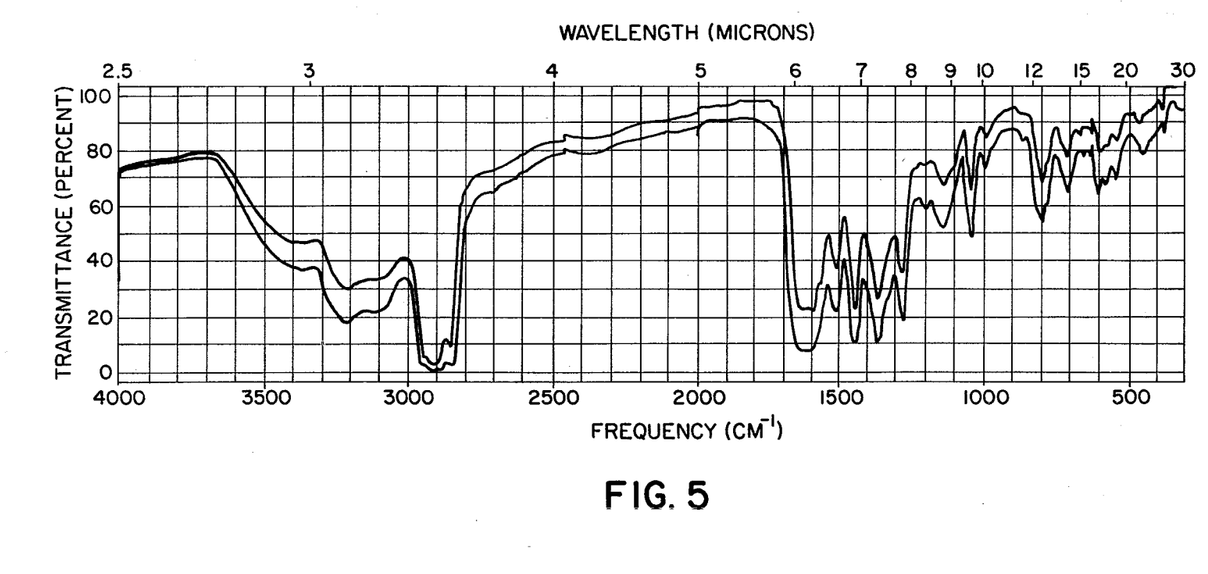
Figure 6:
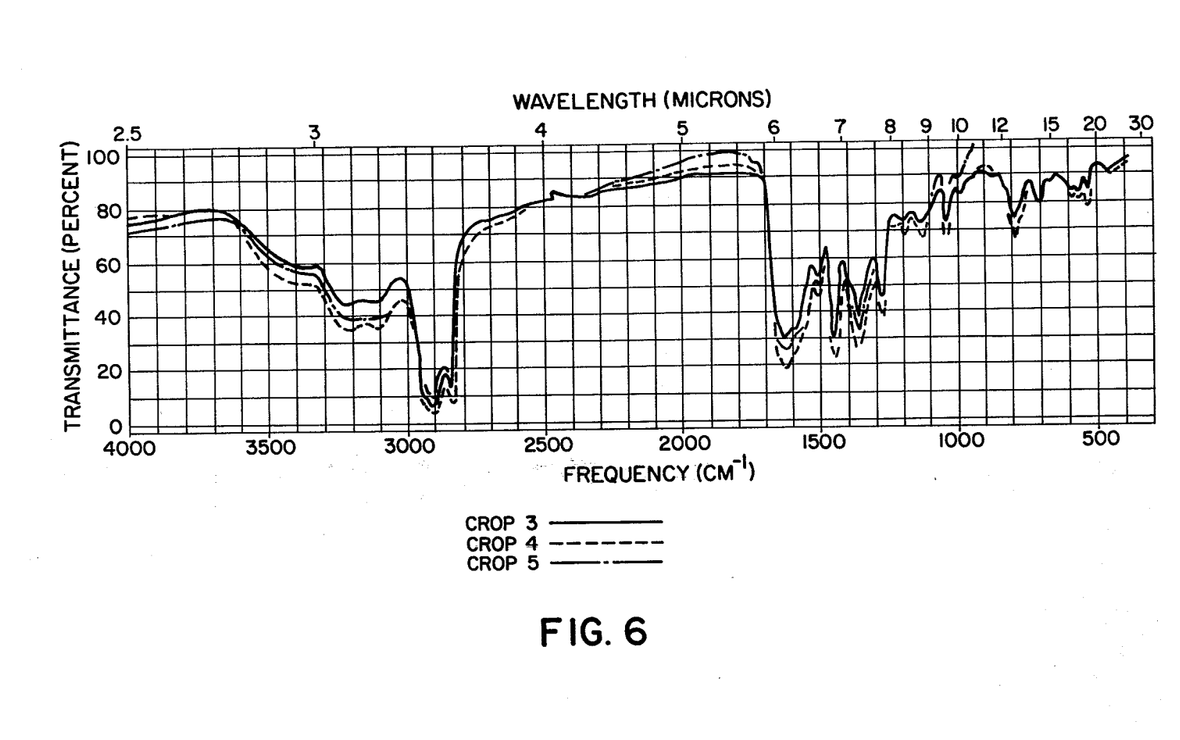

The complete ultraviolet spectra for each of crops 1 and 2 of Example II are reproduced in FIG. 3, and for crops 3, 4, 5 and 6 of Example II are reproduced in FIG. 4. The infra-red spectra for crops 1 and 2 of Example II are shown in FIG. 5, in which the upper curve is for crop 1 and the lower curve is for crop 2, and the infra-red spectra for crops 3, 4 and 5 of Example II are shown in FIG. 6.

Unlike the so-called "platinum-blues", the "platinum tans" of this invention have two prominent absorption bands below 300 nm but do not possess characteristic maxima above 400 nm which characterize the "platinum blues".

By the term "saccharide moiety" as employed herein is meant the residue of the pentose or hexose having the formula:

where $x=2$ or 3 when Z is hydrogen or phosphato. Residues of, for example, ribofuranose, glucose and phosphato derivatives thereof are useful.

What is claimed is:

1. An ethylenediamineplatinum(II) 2,4-dioxopyrimidine complex consisting of a 2,4-dioxopyrimidine moiety and an ethylenediamineplatinum(II) moiety wherein the 2,4-dioxopyrimidine moiety has the formula:

wherein R is a saccharide moiety which is the residue of a pentose or hexose having the formula:

wherein $x=2$ or 3 when Z is hydrogen or phosphato, and each of $R^1$ and $R^2$, independently is hydrogen, halogen, lower alkyl, carboxyl, lower alkoxycarbonyl, hydroxy, and lower alkoxy, and the dihydro derivatives of said 2,4-dioxopyrimidines, and the ethylenediamine moiety has the formula:

wherein each of $R^3$, $R^4$, $R^5$, $R^6$, $R^7$ and $R^8$, when taken separately, is hydrogen or lower alkyl, the ultraviolet spectrum of said complex being characterized by absorption maxima at about 200 nm and about 288 nm and an absorption minimum at about 254 nm.

2. A complex according to claim 1 wherein each of $R^3$-$R^8$ is hydrogen.

3. A complex according to claim 2 wherein each of $R^1$ and $R^2$ is hydrogen.

4. A complex according to claim 2 wherein R' is hydrogen and $R^2$ is methyl.

5. A complex according to claim 2 wherein $R^1$ and $R^2$ are hydrogen and R is ribosyl.

6. A complex according to claim 2, wherein $R^1$ is hydrogen, $R^2$ is methyl, and R is ribosyl.

* * * * *

UNITED STATES PATENT AND TRADEMARK OFFICE
CERTIFICATE OF CORRECTION

PATENT NO. : 4,207,416
DATED : June 10, 1980
INVENTOR(S) : James D. Hoeschele

It is certified that error appears in the above-identified patent and that said Letters Patent are hereby corrected as shown below:

In column 1, line 43, insert --"-- after the word "tan";

Column 6, line 12, change "arbitarily" to --arbitrarily--;

Column 6, line 49, change "km/kg" to --mg/kg--;

Column 7, line 37, change "actue" to --acute--;

Column 8, line 62, Claim 4, change "R'" to --$R^1$--.

Signed and Sealed this

Seventh Day of April 1981

[SEAL]

Attest:

RENE D. TEGTMEYER

Attesting Officer     Acting Commissioner of Patents and Trademarks